United States Patent [19]

Marler et al.

[11] Patent Number: 5,105,023
[45] Date of Patent: Apr. 14, 1992

[54] PROCESS FOR THE HYDRATION OF OLEFINS CROSS REFERENCE TO RELATED APPLICATIONS

[75] Inventors: David O. Marler, Deptford, N.J.; Charles M. Sorensen, Wilmington, Del.; Philip Varghese, Voorhees, N.J.

[73] Assignee: Mobil Oil Corp., Fairfax, Va.

[21] Appl. No.: 279,615

[22] Filed: Dec. 5, 1988

Related U.S. Application Data

[63] Continuation-in-part of Ser. No. 139,557, Dec. 30, 1987, abandoned.

[51] Int. Cl.$^5$ .................... C07C 41/05; C07C 29/04
[52] U.S. Cl. .................... 568/695; 568/694; 568/897
[58] Field of Search .................... 568/694, 695, 897

[56] References Cited

U.S. PATENT DOCUMENTS

| | | |
|---|---|---|
| 3,493,518 | 2/1970 | Jonassen et al. |
| 4,214,107 | 7/1980 | Chang et al. |
| 4,439,409 | 3/1984 | Puppe et al. |
| 4,499,313 | 2/1985 | Okumura et al. |
| 4,611,086 | 9/1986 | Geuguen et al. |

FOREIGN PATENT DOCUMENTS

| | | |
|---|---|---|
| 210793 | 2/1987 | European Pat. Off. |
| 246335 | 12/1985 | Japan |

*Primary Examiner*—Howard T. Mars
*Attorney, Agent, or Firm*—Alexander J. McKillop; Charles J. Speciale; Dennis P. Santini

[57] ABSTRACT

A process for converting light olefin to alcohol(s), ether(s) or mixtures of alcohol(s) and ether(s) which comprises contacting a feed containing at least one light olefin with water in the vapor and/or liquid phase under olefin hydration conditions in the presence of acidic zeolite MCM-22 as olefin hydration catalyst to produce said alcohol(s) and/or ether(s).

23 Claims, 3 Drawing Sheets

PROCESS FOR THE HYDRATION OF OLEFINS CROSS REFERENCE TO RELATED APPLICATIONS

CROSS REFERENCE TO RELATED APPLICATIONS

This application is a continuation-in-part of U.S. patent application Ser. No. 139,557, filed Dec. 30, 1987, abandoned.

BACKGROUND OF THE INVENTION

This invention relates to a process for the catalytic hydration of olefins to provide alcohols, ethers or their mixtures. More particularly, the invention relates to a process for the hydration of light olefins such as ethylene, propylene, butenes, pentenes, hexenes, heptenes, etc., and their mixtures to provide alcohols and/or ethers employing the acidic form of the synthetic porous crystalline material, or zeolite, MCM-22 as catalyst. The alcohols and/or ethers are useful, inter alia, as high octane blending stocks for gasoline.

There is a need for an efficient catalytic process to manufacture alcohols and ethers from light olefins thereby augmenting the supply of high octane blending stocks for gasoline. Lower molecular weight alcohols and ethers such as isopropyl alcohol (IPA) and diisopropyl ether (DIPE) are in the gasoline boiling range and are known to have a high blending octane number. In addition, by-product propylene from which IPA and DIPE can be made is usually available in a fuels refinery. The petrochemicals industry also produces mixtures of light olefin streams in the $C_2$ to $C_7$ molecular weight range and the conversion of such streams or fractions thereof to alcohols and/or ethers can also provide products useful as solvents and as blending stocks for gasoline.

The catalytic hydration of olefins to provide alcohols and ethers is a well-established art and is of significant commercial importance. Representative olefin hydration processes are disclosed in U.S. Pat. Nos. 2,162,913; 2,477,380; 2,797,247; 3,798,097; 2,805,260; 2,830,090; 2,861,045; 2,891,999; 3,006,970; 3,198,752; 3,810,849; and, 3,989,762, among others.

Olefin hydration employing zeolite catalysts is known. As disclosed in U.S. Pat. No. 4,214,107, lower olefins, in particular, propylene, are catalytically hydrated over a crystalline aluminosilicate zeolite catalyst having a silica to alumina ratio of at least 12 and a Constraint Index of from 1 to 12, e.g., HZSM-5 type zeolite, to provide the corresponding alcohol, essentially free of ether and hydrocarbon by-product.

According to U.S. Pat. No. 4,499,313, an olefin is hydrated to the corresponding alcohol in the presence of hydrogen-type mordenite or hydrogen-type zeolite Y each having a silica-alumina molar ratio of 20 to 500. The use of such a catalyst is said to result in higher yields of alcohol than olefin hydration processes which employ conventional solid acid catalysts. Use of the catalyst is said to offer the advantage over ion-exchange type olefin hydration catalysts of not being restricted by the hydration temperature. Reaction conditions employed in the process include a temperature of from 50°-300° C., preferably 100°-250° C., a pressure of 5 to 200 kg/cm² to maintain liquid phase or gas-liquid multiphase conditions and a mole ratio of water to olefin of from 1 to 20. The reaction time can be 20 minutes to 20 hours when operating batchwise and the liquid hourly space velocity (LHSV) is usually 0.1 to 10 in the case of continuous operation.

U.S. Pat. No. 4,611,086 describes the hydration of olefins to provide aliphatic alcohols employing natural or synthetic offretite as catalyst.

European Patent Application 210,793 describes an olefin hydration process employing a medium pore zeolite as hydration catalyst. Specific catalysts mentioned are Theta-1, said to be preferred, ferrierite, ZSM-22, ZSM-23 and NU-10.

Japanese laid-open application 60-246,335 describes the hydration of branched olefins in the presence of finely powdered zeolite catalyst.

SUMMARY OF THE INVENTION

It is an object of this invention to provide an efficient process of catalytic hydration for converting economical, readily available sources of light olefins to alcohol(s), ether(s) or mixtures thereof which are useful as high octane blending stocks for gasoline.

It is a particular object of the invention to provide a process for catalytically hydrating olefin(s) to provide alcohol(s) and/or ether(s) employing acidic zeolite MCM-22 as catalyst.

It is a further particular object of this invention to co-produce isopropyl alcohol (IPA) and diisopropyl ether (DIPE) by catalytically hydrating propylene over acidic zeolite MCM-22 catalyst.

By way of realizing the foregoing and other objects of the invention, a process for converting light olefin to alcohol(s) and/or ether(s) is provided which comprise contacting a feed consisting essentially of at least one light olefin with water and an olefin hydration catalyst in the vapor and/or liquid phase under olefin hydration conditions to provide said mixture of alcohol(s) and/or ether(s), said olefin hydration catalyst comprising a synthetic porous crystalline material characterized by an X-ray diffraction pattern substantially as set forth in Table I of the specification and having a composition comprising the molar relationship:

$$X_2O_3:(n)YO_2$$

wherein X is a trivalent element, Y is a tetravalent element and n is at least about 10.

The alcohol(s), ether(s) or mixtures thereof resulting from the foregoing olefin hydration process are advantageously employed as blending components for gasoline and as cosolvents for methanol to be incorporated into gasoline among other applications.

DESCRIPTION OF THE PREFERRED EMBODIMENTS

The present invention is applicable to the hydration of individual light olefins and mixtures of olefins of various structures, preferably within the $C_{2-7}$ range. Accordingly, the invention is applicable to the hydration of mixtures of ethylene, propylene, butenes, pentenes, heptenes, mixtures of these and other olefins such as gas plant off-gas containing ethylene and propylene, naphtha cracker off-gas containing light olefins, fluidized catalytic cracked (FCC) light gasoline containing pentenes, hexenes and heptenes, refinery FCC propane/propylene streams, etc. For example a typical FCC light olefin stream possesses the following composition:

| Typical Refinery FCC Light Olefin Composition | | |
|---|---|---|
| | Wt. % | Mole % |
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

The process of the invention is especially applicable to the conversion of propylene to mixtures of IPA and DIPE.

The operating conditions of the olefin hydration process herein are not especially critical and include a temperature of from about 50° to 300° C., preferably from about 90° to about 250° C. and most preferably from about 110° to about 220° C., a total system pressure of at least from about 5 atmospheres and preferably at least about 20 atmospheres and water to olefin mole ratio of from about 0.1 to about 30, preferably from about 0.2 to about 15 and most preferably from about 0.3 to about 5.

The olefin hydration process of this invention can be carried out under liquid phase, vapor phase or mixed vapor-liquid phase conditions in batch or continuous manner using a stirred tank reactor or fixed bed flow reactor, e.g., trickle-bed, liquid-up-flow, liquid-down-flow, counter-current, co-current, etc. Reaction times of from about 20 minutes to about 20 hours when operating in batch and an LHSV of from about 0.1 to about 10 when operating continuously are suitable. It is generally preferable to recover any unreacted olefin and recycle it to the reactor.

The synthesis porous crystalline material employed as catalyst in the olefin hydration process of this invention, referred to herein as "zeolite MCM-22" or simply "MCM-22", appears to be related to the composition named "PSH-3" described in U.S. Pat. No. 4,439,409. Zeolite MCM-22 does not appear to contain all the components apparently present in the PSH-3 compositions. Zeolite MCM-22 is not contaminated with other crystal structures, such as ZSM-12 or ZSM-5, and exhibits unusual sorption capacities and unique catalytic utility when compared to the PSH-3 compositions synthesized in accordance with U.S. Pat. No. 4,439,409.

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

wherein R is an organic component. The Na and R components are associated with the zeolite as a result of their presence during crystallization, and are easily removed by post-crystallization methods hereinafter more particularly described.

Zeolite MCM-22 is thermally stable and exhibits high surface area (greater than 400 m²/gm as measured by the BET [Bruenauer, Emmet and Teller] test) and unusually large sorption capacity when compared to previously described crystal structures having similar X-ray diffraction patterns. As is evident from the above formula, MCM-22 is synthesized nearly free of Na cations. It can, therefore, be used as an olefin hydration catalyst with acid activity without an exchange step. To the extent desired, however, the original sodium cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the activity of the catalyst for olefin hydration. These include hydrogen, rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern which is distinguished from the patterns of other known crystalline materials by the lines listed in Table I below:

TABLE I

| Interplanar d-Spacing (A) | Relative Intensity, I/Io × 100 |
|---|---|
| 30.0 ± 2.2 | W-M |
| 22.1 ± 1.3 | W | more specifically by the lines listed in Table II below:

TABLE II

| Interplanar d-Spacing (A) | Relative Intensity, I/Io × 100 |
|---|---|
| 30.0 ± 2.2 | W-M |
| 22.1 ± 1.3 | W |
| 3.91 ± 0.07 | M-VS | and yet more specifically by the lines listed in Table III below:

TABLE III

| Interplanar d-Spacing (A) | Relative Intensity, I/Io × 100 |
|---|---|
| 30.0 ± 2.2 | W-M |
| 22.1 ± 1.3 | W |
| 6.00 ± 0.01 | W-M |
| 4.06 ± 0.07 | W-S |
| 3.91 ± 0.07 | M-VS |

Most specifically, the calcined crystalline material has an X-ray diffraction pattern which includes the lines listed in Table IV below:

TABLE IV

| Interplanar d-Spacing (A) | Relative Intensity, I/Io × 100 |
|---|---|
| 30.0 ± 2.2 | W-M |
| 22.1 ± 1.3 | W |
| 12.36 ± 0.2 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |

TABLE IV-continued

| Interplanar d-Spacing (A) | Relative Intensity, I/Io × 100 |
|---|---|
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 I/$I_o$, where $I_o$ is the intensity of the strongest line or peak, and d (obs.) the interplanar spacing in Angstroms Units (A), corresponding to the recorded lines, were determined. In Tables I-IV, the relative intensities are given in terms of the symbols W=weak, M=medium, S=strong and VS=very strong. In terms of intensities, these may be generally designated as follows:

W=0-20
M=20-40
S=40-60
VS=60-100

It should be understood that these X-ray diffraction patterns are characteristic of all species of the present crystalline composition. The sodium form as well as other cationic forms reveal substantially the same pattern with some minor shifts in interplanar spacing and variation in relative intensity. Other minor variations can occur depending on the Y to X, e.g., silicon to aluminum, mole ratio of the particular sample, as well as its degree of thermal treatment.

Prior to its use as olefin hydration catalyst, the MCM-22 crystals should be subjected to thermal treatment to remove part or all of any organic constituent present therein.

The zeolite MCM-22 olefin hydration catalyst herein can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be introduced in the catalyst composition by way of cocrystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing a platinum metal-containing ion. Thus, suitable platinum compounds for this purpose include chloroplatinic acid, platinous chloride and various compounds containing the platinum amine complex.

Zeolite MCM-22, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use in the olefin hydration process of this invention, the zeolite MCM-22 crystals should be dehydrated, at least partially. This can be done by heating the crystals to a temperature in the range of from about 200° C. to about 595° C. in an inert atmosphere, such as air, nitrogen, etc. and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

Zeolite MCM-22 can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10-80 | 10-60 |
| $H_2O/YO_2$ | 5-100 | 10-50 |
| $OH^-/YO_2$ | 0.01-1.0 | 0.1-0.5 |
| $M/YO_2$ | 0.01-2.0 | 0.1-1.0 |
| $R/YO_2$ | 0.05-1.0 | 0.1-0.5 |

In a preferred method of synthesizing zeolite MCM-22, the $YO_2$ reactant contains a substantial amount of solid $YO_2$, e.g., at least about 30 wt. % solid $YO_2$ Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystal formation from the above mixture and is a distinct improvement over the synthesis method disclosed in U.S. Pat. No. 4,439,409. If another source of oxide of silicon, e.g., Q-Brand (a sodium silicate comprised of about 28.8 wt. % of $SiO_2$, 8.9 wt. % $Na_2O$ and 62.3 wt. % $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt. % solid $YO_2$, e.g., silica, and more preferably at least about 40 wt. % solid $YO_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine which has the following structural formula:

It should be realized that the reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals (based on total weight) of the crystalline product.

The MCM-22 crystals can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

It may be desired to incorporate the MCM-22 crystalline material with another material which is resistant to the temperatures and other conditions employed in the olefin hydration process of this invention. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with zeolite MCM-22, i.e., combined therewith or present during its synthesis, which itself is catalytically active may change the conversion and/or selectivity of the catalyst. Inactive materials suitably serve as diluents to control the amount of conversion so that olefin hydration products can be obtained economically and orderly without employing other means for controlling the rate of reaction. These materials may be incorporated into naturally occurring clays, e.g., bentonite and kaolin, to improve the crush strength of the catalyst under commercial olefin oligomerization operating conditions. Said materials, i.e., clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with MCM-22 crystals include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with zeolite MCM-22 also include inorganic oxides, notably alumina.

In addition to the foregoing materials, the MCM-22 crystals can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided crystalline material and inorganic oxide matrix vary widely with the crystal content ranging from about 1 to about 90 percent by weight and more usually, particularly when the composite is prepared in the form of beads, in the range of about 2 to about 80 weight percent of the composite.

The stability of zeolite MCM-22 may be increased by combining the as-synthesized MCM-22 with an alumina binder, converting the alumina-bound MCM-22 to the hydrogen form, (i.e., (HMCM-22) and steaming the alumina-bound HMCM-22 composition under conditions sufficient to increase the stability of the catalyst. U.S. Pat. Nos. 4,663,492; 4,594,146; 4,522,929; and, 4,429,176, the entire disclosures of which are incorporated herein by reference, describe conditions for the steam stabilization of zeolite catalysts which can be utilized to steam-stabilize alumina-bound HMCM-22. The steam stabilization conditions include contacting the alumina bound HMCM-22 with, e.g., 5-100% steam at a temperature of at least about 300° C. (e.g., 300°-650° C.) for at least one hour (e.g., 1-200 hours) at a pressure of 101-2,500 kPa. In a more particular embodiment, the catalyst can be made to undergo steaming with 75-100% steam at 315°-500° C. and atmospheric pressure for 2-25 hours. In accordance with the steam stabilization treatment described in the above-mentioned patents, the steaming of the catalyst can take place under conditions sufficient to initially increase the Alpha Value of the catalyst, the significance of which is discussed infra, and produce a steamed catalyst having a peak Alpha Value. If desired, steaming can be continued to subsequently reduce the Alpha Value from the peak Alpha Value to an Alpha Value which is substantially the same as the Alpha Value of the unsteamed catalyst.

In order to more fully illustrate the olefin hydration process of this invention and the manner of practicing same, the following examples are presented. In Examples 1 to 14 which are illustrative of the synthesis of zeolite MCM-22, whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm and contacted with 12 Torr of water vapor and 40 Torr of n-hexane or cyclohexane vapor, pressures less than the vapor-liquid equilibrium pressure of the respective adsorbate at 90° C. The pressure was kept constant (within about ±0.5 mm) by addition of adsorbate vapor controlled by a manostat during the adsorption period, which did not exceed about 8 hours. As adsorbate was adsorbed by the MCM-22 crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM-22 always exhibits Equilibrium Adsorption values of greater than about 10 wt. % for water vapor, greater than about 4.5 wt. %, usually greater than about 7 wt. % for cyclohexane vapor and greater than about 10 wt. % for n-hexane vapor. These vapor sorption capacities are a notable distinguishing feature of zeolite MCM-22.

When Alpha Value is examined, it is noted that the Alpha Value is an approximate indication of the catalytic cracking activity of the catalyst compared to a standard catalyst and it gives the relative rate constant (rate or normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 4,016,218 and in *J. Catalysis*, 6, pp. 278-287 (1966) and *J. Catalysis*, 61, pp. 390-396 (1980) each of which is incorporated by reference herein as to that description. It is noted that intrinsic rate constants for many acid-catalyzed reactions are proportional to the Alpha Value for a particular crystalline silicate catalyst, i.e., the rates for toluene disproportionation, xylene isomerization, alkene conversion and methanol conversion (see "The Active Side of Acidic Aluminosilicate Catalysts," *Nature*, Vol. 309, No. 5969, pp. 589-591, 14 June 1984).

EXAMPLE 1

Sodium aluminate (43.5% $Al_2O_3$, 32.2% $Na_2O$, 25.6% $H_2O$), 12.86, was dissolved in a solution containing 12.8 g 50% NaOH solution and 1320 g $H_2O$. To this was added 57.6 g hexamethyleneimine. The resulting solution was added to 109.4 g of Ultrasil, a precipitated, spray-dried silica (about 90% $SiO_2$).

The reaction mixture had the following composition, in mole ratios:

$SiO_2/Al_2O_3 = 30.0$
$OH^-/SiO_2 = 0.18$
$H_2O/SiO_2 = 44.9$
$Na/SiO_2 = 0.18$
$R/SiO_2 = 0.35$ where R is hexamethyleneimine.

Figure 1:
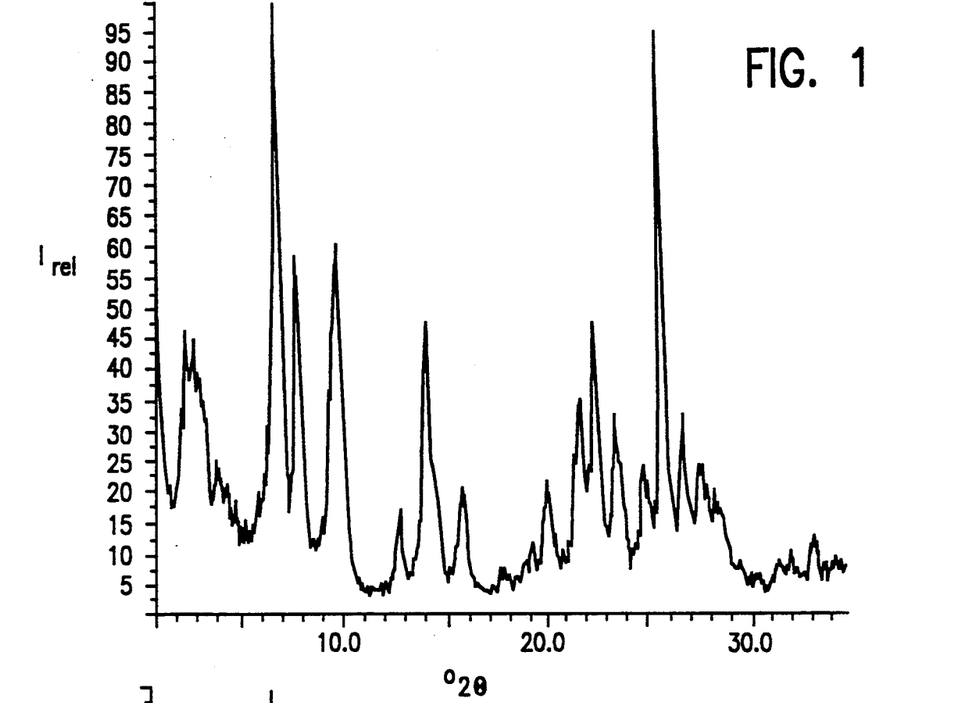
FIGS. 1-5 are X-ray diffraction patterns of the calcined crystalline material products of Examples 1, 3, 4, 5 and 7, respectively, hereinafter presented.

The mixture was crystallized in a stainless steel reactor, with stirring, at 150° C. for 7 days. The crystalline product was filtered, washed with water and dried at 120° C. After a 20 hour calcination at 538°, the X-ray diffraction pattern contained the major lines listed in Table V. FIG. 1 shows the X-ray diffraction pattern of the calcined product. The sorption capacities of the calcined material were measured to be:

$H_2O$ (12 Torr) 15.2 wt. %
Cyclohexane (40 Torr) 14.6 wt. %
n-Hexane (40 Torr) 16.7 wt. %

The surface area of the calcined crystalline material was measured to be 494 m$^2$/g.

The chemical composition of the calcined material was determined to be as follows:

| Component | wt. % |
|---|---|
| $SiO_2$ | 66.9 |
| $Al_2O_3$ | 5.40 |
| Na | 0.03 |
| N | 2.27 |
| Ash | 76.3 |

$SiO_2/Al_2O_3$, mole ratio - 21.1

TABLE V

| Degrees 2-Theta | Interplanar d-Spacing (A) | I/I$_o$ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3-5

Figure 2:
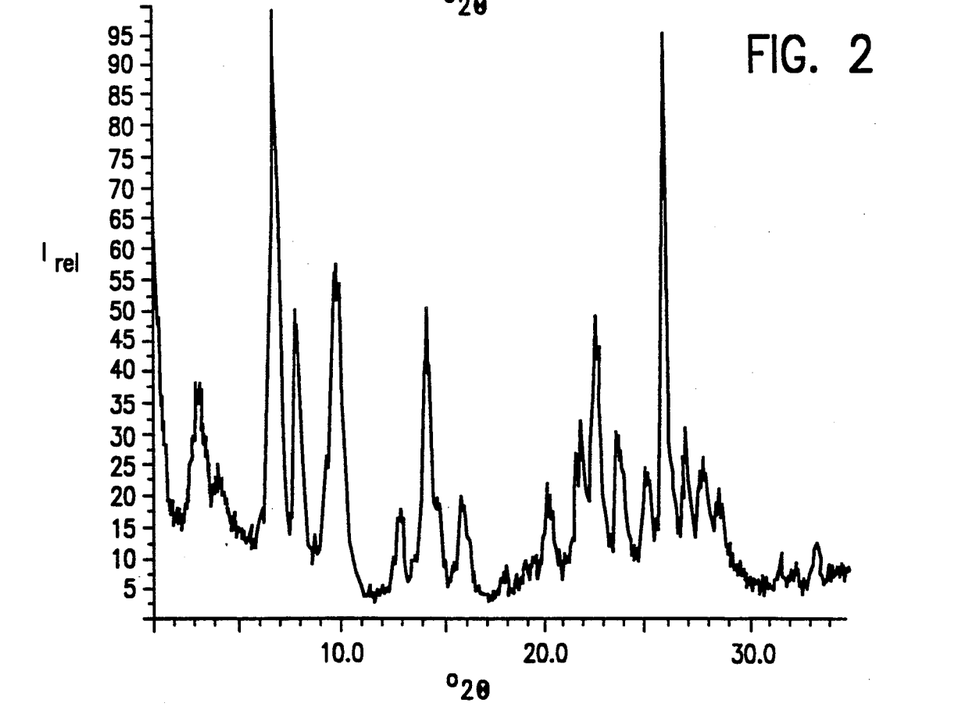
Figure 3:
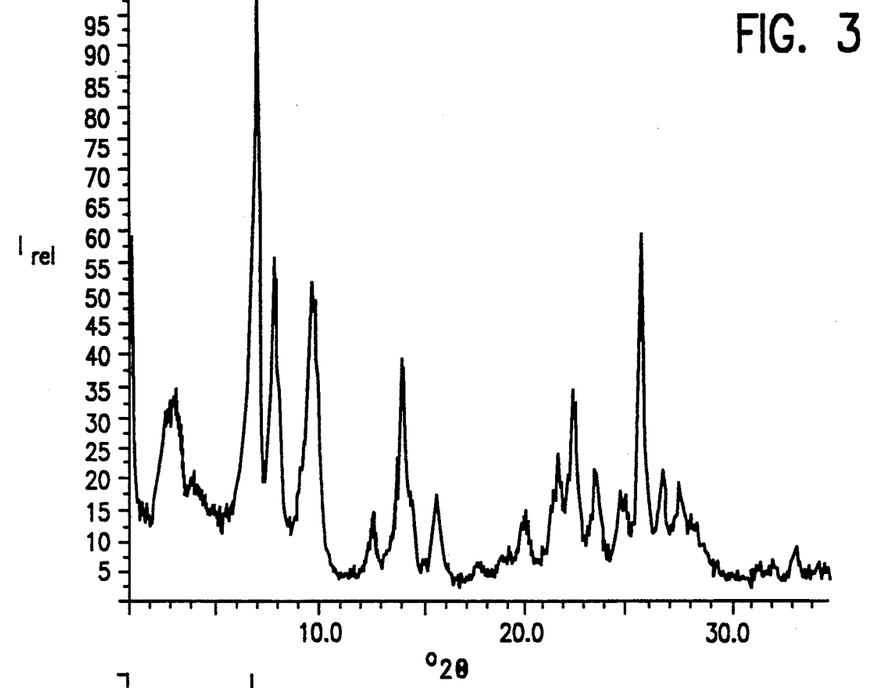
Figure 4:
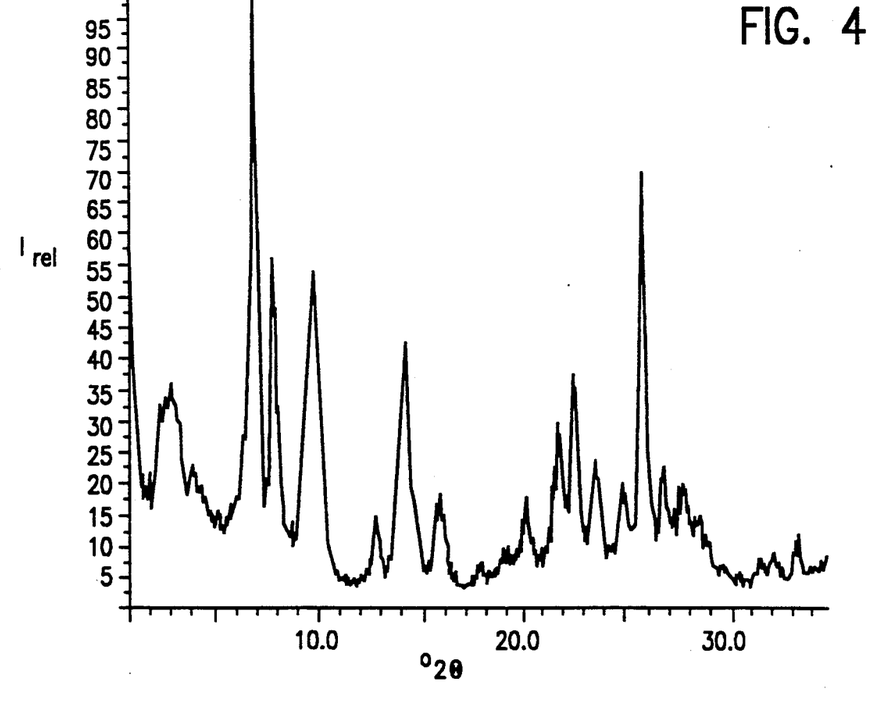

Three separate synthesis reaction mixtures were prepared with compositions indicated in Table VI. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days, respectively, in a stainless steel, stirred (350 rpm) autoclave at autogenous pressure. Solids were separated from any unreacted components by filtration and then water washed, followed by drying at 120° C. The product crystals were analyzed by X-ray diffraction, sorption, surface area and chemical analyses and found to be crystalline material referred to herein as zeolite MCM-22. Results of sorption, surface area and chemical analyses are also presented in Table VI. The X-ray diffraction patterns are presented in FIGS. 2, 3 and 4, respectively. The sorption and surface area measurements were of the calcined product.

TABLE VI

| | Example | | |
|---|---|---|---|
| | 3 | 4 | 5 |
| Synthesis Mixture, mole ratios | | | |
| $SiO_2/Al_2O_3$ | 30.0 | 30.0 | 30.0 |

TABLE VI-continued

|  | Example | | |
|---|---|---|---|
|  | 3 | 4 | 5 |
| OH⁻/SiO₂ | 0.18 | 0.18 | 0.18 |
| $H_2O/SiO_2$ | 19.4 | 19.4 | 44.9 |
| $Na/SiO_2$ | 0.18 | 0.18 | 0.18 |
| $R/SiO_2$ | 0.35 | 0.35 | 0.35 |
| Product Composition, Wt. % | | | |
| $SiO_2$ | 64.3 | 68.5 | 74.5 |
| $Al_2O_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| $SiO_2/Al_2O_3$, mole ratio | 22.5 | 20.9 | 26.0 |
| Adsorption, Wt. % | | | |
| $H_2O$ | 14.9 | 13.6 | 14.6 |
| Cyclohexane | 12.5 | 12.2 | 13.6 |
| n-Hexane | 14.6 | 16.2 | 19.0 |
| Surface Area, $n^2/g$ | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a larger preparation of zeolite MCM-22, 1200 g of hexamethyleneimine was added to a solution containing 268 g of sodium aluminate, 267 g of 50% NaOH solution and 11,800 g of $H_2O$. To the combined solution was added 2,280 g of Ultrasil silica. The mixture was crystallized with agitation (about 200 rpm) at 145° C. in a 5 gallon reactor. Crystallization time was 59 hours. The product was water washed and dried at 120° C.

Figure 5:
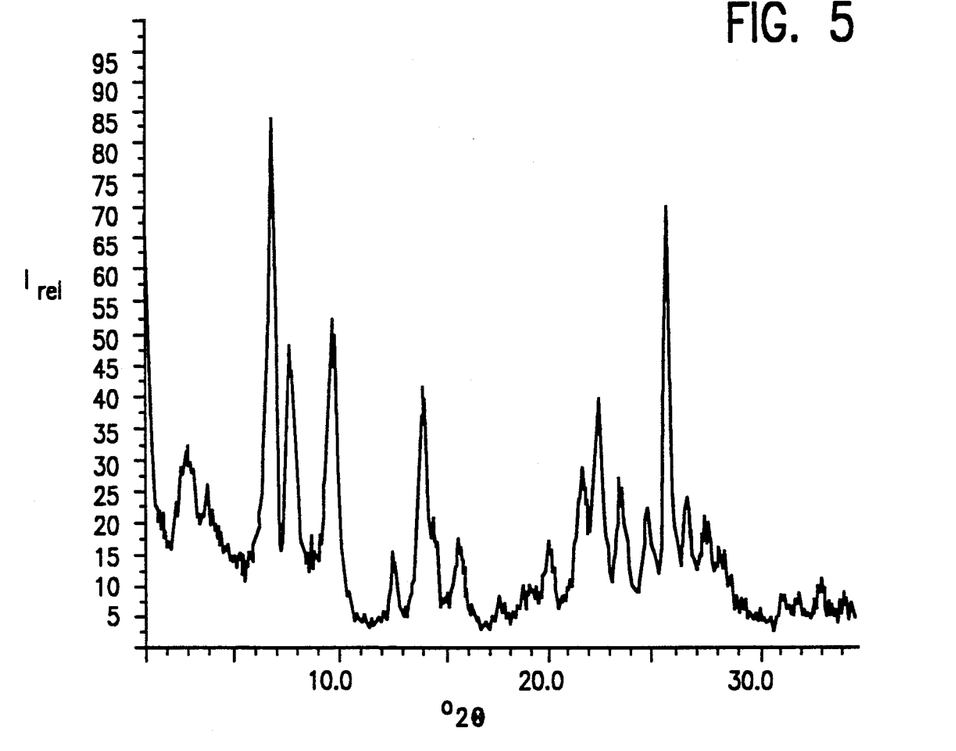

The X-ray diffraction pattern of the dried product crystals is presented in FIG. 5 and demonstrates the product to be the crystalline material of this invention. Product chemical composition, surface area and adsorption analyses results were as set forth in Table VII:

TABLE VII

| Product Composition | |
|---|---|
| C | 12.1 wt. % |
| N | 1.98 wt. % |
| Na | 640 ppm |
| $Al_2O_3$ | 5.0 wt. % |
| $SiO_2$ | 74.9 wt. % |
| $SiO_2/Al_2O_3$, mole ratio | 25.4 |
| Adsorption, wt. % | |
| Cyclohexane | 9.1 |
| N-Hexane | 14.9 |
| $H_2O$ | 16.8 |
| Surface Area, $m^2/g$ | 479 |

EXAMPLE 8

25 g grams of solid crystal product from Example 7 were calcined in a flowing nitrogen atmospheres at 538° C. for 5 hours, followed by purging with 5% oxygen gas (balance $N_2$) for another 16 hours at 538° C.

Individual 3 g samples of the calcined material were ion-exchanged with 100 ml of 0.1N TEABr, TPABr and LaCl₃ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| Exchange Ions Ionic Composition, wt. % | TEA | TPA | La |
|---|---|---|---|
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 10 was severely steamed at 649° C. in 100% steam for 2 hours. The steamed sample had an Alpha Value of 22, demonstrating that the zeolite MCM-22 has very good stability under severe hydrothermal treatment.

EXAMPLE 11

This example illustrates the preparation of zeolite MCM-22 where X in the general formula, supra, is boron. Boric acid, 17.5 g, was added to a solution containing 6.75 g of 45% KOH solution and 290 g $H_2O$. To this was added 57.8 g of Ultrasil silica, and the mixture was thoroughly homogenized. A 26.2 g quantity of hexamethyleneimine was added to the mixture.

The reaction mixture had the following composition in mole ratios:

$SiO_2/B_2O_3 = 6.1$
$OH^-/SiO_2 = 0.06$
$H_2O/SiO_2 = 19.0$
$K/SiO_2 = 0.06$
$R/SiO_2 = 0.30$ where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 540° C. and found to have the following sorption capacities:

$H_2O$ (12 Torr) 11.7 wt. %
Cyclohexane (40 Torr) 7.5 wt. %
n-Hexane (40 Torr) 11.4 wt. %

The surface area of the calcined crystalline material was measured (BET) to be 405 $m^2/g$.

The chemical composition of the calcined material was determined to be as follows:

N: 1.94 wt. %
Na: 175 ppm
K: 0.60 wt. %
Boron: 1.04 wt. %
$Al_2O_3$: 920 ppm
$SiO_2$: 75.9 wt. %
Ash: 74.11 wt. %
$SiO_2/Al_2O_3$, molar ratio = 1406
$SiO_2/(Al+B)_2O_3$, molar ratio = 25.8

EXAMPLE 12

A portion of the calcined crystalline product of Example 11 was treated with NH₄Cl and again calcined.

The final crystalline product was tested in the Alpha Test and found to have an Alpha Value of 1.

EXAMPLE 13

This example illustrates another preparation of zeolite MCM-22 in which X of the general formula, supra, is boron. Boric acid, 35.0 g, was added to a solution of 15.7 g of 50% NaOH solution and 1160 g $H_2O$. To this solution was added 240 g of HiSil silica followed by 105 g of hexamethyleneimine. The reaction mixture had the following composition in mole ratios:

$SiO_2/B_2O_3 = 12.3$
$OH^-/SiO_2 = 0.056$
$H_2O/SiO_2 = 18.6$
$K/SiO_2 = 0.056$
$R/SiO_2 = 0.30$ where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

$H_2O$ (12 Torr) 14.4 wt. %
Cyclohexane (40 Torr) 4.6 wt. %
n-Hexane (40 Torr) 14.0 wt. %

The surface area of the calcined crystalline material was measured to be 438 m$^2$/g.

The chemical composition of the calcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |

$SiO_2/Al_2O_3$, molar ratio = 249
$SiO_2/(Al + B)_2O_3$, molar ratio = 28.2

EXAMPLE 14

A portion of the calcined crystalline product of Example 13 was tested in the Alpha Test and found to have an Alpha Value of 5.

EXAMPLE 15

This example illustrates the preparation of alumina-bound acidic zeolite ZSM-35, the use of which as olefin hydration catalyst is outside the scope of this invention, and zeolite MCM-22 whose use as olefin hydration catalyst forms the subject matter of this invention.

A. Preparation of ZSM-35

Pyrrolidine in an amount of 3.2 weight parts was added to a mixture of 1.38 weight parts 50 weight percent aqueous sodium hydroxide, 1.18 weight parts of hydrated aluminum sulfate ($Al_2O_3(SO_4)_3 \cdot 14H_2O$), 3.2 weight parts amorphous precipitated silica (PPG Industries HiSil 233) and 7.5 weight parts deionized water. The reaction mixture was then heated to 220° F. and stirred in an autoclave at that temperature for crystallization. After full crystallinity was achieved, the resulting crystals were separated from remaining liquid by filtration, washed with water and dried. Analysis of the crystals confirmed the presence of zeolite ZSM-35.

A portion of the crystals was combined with alumina to form a mixture of 65 weight parts zeolite ZSM-35 and 35 weight parts alumina. Enough water was added to the mixture so that the resulting catalyst could be formed into extrudate. The catalyst was activated by calcining first in nitrogen at 1000° F., followed by aqueous exchanges with 1.0N ammonium nitrate solution and calcining in air at 1000° and 1200° F.

B. Preparation of MCM-22

Hexamethyleneimine in an amount of 15.9 weight parts was added to a mixture of 3.5 weight parts 50 weight percent aqueous sodium hydroxide, 3.5 weight parts of sodium aluminate, 30.1 weight parts of amorphous precipitated silica (Degussa Corporation Ultrasil VN3) and 156 weight parts deionized water. The reaction mixture was heated directly to 290° F. and stirred in an autoclave at that temperature for crystallization. After full crystallinity was achieved, the resulting crystals were separated from remaining liquid by filtration, washed with water and dried. Analysis of the crystals confirmed the presence of zeolite MCM-22.

A portion of the crystals was combined with alumina to form a mixture of 65 weight parts zeolite MCM-22 and 35 parts alumina. Enough water was added to this mixture so that the resulting catalyst could be formed into an extrudate. This catalyst was activated by calcining in nitrogen at 1000° F., followed by aqueous 1.0N ammonium nitrate exchange and calcining in air at 1000° and 1200° F.

EXAMPLE 16

The alumina-bound acidic zeolite MCM-22 of Example 15 was employed as catalyst for the hydration of propylene to provide mixtures of IPA and DIPE under the conditions and with the results set forth in Table VIII as follows:

TABLE VIII

| REACTION CONDITIONS | | | | | |
|---|---|---|---|---|---|
| Reactor Pressure (psig) | 1000.00 | 1000.00 | 1000.00 | 1000.00 | 1000.00 |
| Average Temperature (Deg. F.) | 330.00 | 330.00 | 330.00 | 380.00 | 330.00 |
| Oxygen:Propylene Molar Ratio | 2.00 | 0.50 | 1.00 | 2.00 | 0.50 |
| Time on Stream (hr) | 20.25 | 45.00 | 114.25 | 137.50 | 161.50 |
| Space Velocity (WHSV)* | 0.62 | 0.62 | 0.31 | 0.63 | 0.62 |
| Space Velocity (LHSV) | 0.62 | 0.47 | 0.26 | 0.62 | 0.47 |
| MASS BALANCE CLOSURES (%) | | | | | |
| Total Mass Balance | 95.43 | 93.12 | 87.40 | 93.89 | 95.88 |
| Carbon Balance | 94.69 | 91.78 | 85.15 | 92.79 | 95.44 |
| Hydrogen Balance | 95.33 | 92.87 | 87.05 | 93.74 | 95.80 |
| Oxygen Balance | 96.21 | 98.53 | 91.85 | 95.10 | 97.61 |
| FEED COMPOSITION (Wt. %) | | | | | |
| Water | 48.27 | 19.84 | 33.67 | 47.42 | 20.13 |
| Propylene | 51.73 | 80.16 | 66.33 | 52.58 | 79.87 |
| PRODUCT COMPOSITION (Wt. %) | | | | | |
| Water | 38.66 | 13.16 | 27.01 | 41.77 | 15.96 |
| Propylene | 24.10 | 57.92 | 42.06 | 34.55 | 68.08 |

TABLE VIII-continued

| | | | | | |
|---|---|---|---|---|---|
| 2-Propanol | 28.47 | 22.19 | 24.08 | 17.84 | 14.24 |
| Hexenes | 0.46 | 0.04 | 0.27 | 0.69 | 0.20 |
| Isopropyl Ether | 8.31 | 6.69 | 6.59 | 5.15 | 1.52 |
| REACTANT CONVERSIONS (%) | | | | | |
| Total Conversion | 37.24 | 28.92 | 30.94 | 23.68 | 15.96 |
| Water | 19.90 | 33.67 | 19.80 | 11.90 | 20.73 |
| Propylene | 53.42 | 27.75 | 36.59 | 34.30 | 14.76 |
| CONVERSION TO RANGES (%) | | | | | |
| To C3's | 28.47 | 22.19 | 24.08 | 17.84 | 14.24 |
| To C6+ | 8.77 | 6.73 | 6.86 | 5.83 | 1.72 |
| PRODUCT SELECTIVITIES | | | | | |
| 2-Propanol | 76.46 | 76.74 | 77.82 | 75.36 | 89.21 |
| Hexenes | 1.24 | 0.15 | 0.88 | 2.90 | 1.24 |
| Isopropyl Ether | 22.31 | 23.12 | 21.30 | 21.74 | 9.55 |
| PHASE COMPOSITION (Wt. %) | | | | | |
| ETHER PHASE | | | | | |
| Water | 21.25 | 0.00 | 0.00 | 11.42 | 0.00 |
| Propylene | 1.18 | 0.00 | 0.00 | 1.29 | 0.00 |
| 2-Propanol | 47.21 | 0.00 | 0.00 | 40.06 | 0.00 |
| Hexenes | 1.66 | 0.00 | 0.00 | 6.05 | 0.00 |
| Isopropyl Ether | 28.70 | 0.00 | 0.00 | 41.18 | 0.00 |
| Phase Yield on TLP (Wt. %) | 19.19 | 0.00 | 0.00 | 6.26 | 0.00 |
| AQUEOUS PHASE | | | | | |
| Water | 58.74 | 31.68 | 47.45 | 69.73 | 51.74 |
| Propylene | 0.13 | 1.16 | 0.79 | 0.19 | 0.38 |
| 2-Propanol | 36.15 | 57.28 | 43.34 | 27.71 | 47.14 |
| Isopropyl Ether | 4.99 | 9.77 | 8.33 | 2.38 | 0.74 |
| Phase Yield On TLP (Wt. %) | 80.81 | 100.00 | 100.00 | 93.74 | 100.00 |

*WHSV based on propylene and zeolite.

EXAMPLE 17

This examples compares the catalytic performance of zeolite MCM-22 of Example 15 with zeolite Beta (U.S. Reissue Pat. No. 28,341; original U.S. Pat. No. 3,308,069) and zeolite ZSM-35 (U.S. Pat. No. 4,016,345) of Example 15 for the hydration of propylene. Each of the zeolites is bound with 35 weight percent alumina.

The hydration conditions and the results of each hydration operation are set forth in Table IX as follows:

TABLE IX

| | MCM-22 | ZSM-35 | Beta |
|---|---|---|---|
| Hydration Reaction Conditions: 2:1 Mole Ratio of Water:Propylene; 330° F.; 1000 psig | | | |
| Propylene Conversion | 53.4 | 55.1 | 51.0 |
| IPA Selectivity | 76.5 | 99.5 | 48.7 |
| DIPE Selectivity | 22.3 | 0.3 | 48.2 |
| Hydration Reaction Conditions: 0.5:1 Mole Ratio of Water:Propylene; 330° F.; 1000 psig | | | |
| Propylene Conversion | 27.8 | 31.0 | 44.9 |
| IPA Selectivity | 76.7 | 99.3 | 39.8 |
| DIPE Selectivity | 23.1 | 0.4 | 57.3 |

As these data show, the selectivity profile of MCM-22 for the production of IPA and DIPE from propylene consistently and significantly differs from those of ZSM-35 and zeolite Beta.

What is claimed is:

1. A process for converting light olefin to alcohol(s), ether(s) or mixtures thereof which comprises contacting a feed consisting essentially of at least one light olefin with water and an olefin hydration catalyst in the vapor and/or liquid phase under olefins hydration conditions to provide said alcohol(s) and/or ether(s), said olefin hydration catalyst comprising a synthetic porous crystalline material characterized by an X-ray diffraction pattern including values substantially as follows:

| Interplanar d-Spacing (A) | Relative Intensity, I/Io × 100 |
|---|---|
| 30.0 ± 2.2 | W-M |
| 22.1 ± 1.3 | W | and having a composition comprising the molar relationship:

$$X_2O_3:(n)YO_2$$

wherein X is a trivalent element, Y is a tetravalent element and n is at least about 10.

2. The process of claim 1 wherein said synthetic porous crystalline material is characterized by an X-ray diffraction pattern including values substantially as follows:

| Interplanar d-Spacing (A) | Relative Intensity, I/Io × 100 |
|---|---|
| 30.0 ± 2.2 | W-M |
| 22.1 ± 1.3 | W |
| 3.91 ± 0.07 | M-VS |

3. The process of claim 1 wherein said synthetic porous crystalline material is characterized by an X-ray diffraction pattern including values substantially as follows:

| Interplanar d-Spacing (A) | Relative Intensity, I/Io × 100 |
|---|---|
| 30.0 ± 2.2 | W-M |
| 22.1 ± 1.3 | W |
| 6.00 ± 0.01 | W-M |
| 4.06 ± 0.07 | W-S |
| 3.91 ± 0.07 | M-VS |

4. The process of claim 1 wherein said synthetic porous crystalline material is characterized by an X-ray diffraction pattern including values substantially as follows:

| Interplanar d-Spacing (A) | Relative Intensity, $I/I_o \times 100$ |
| --- | --- |
| 30.0 ± 2.2 | W-M |
| 22.1 ± 1.3 | W |
| 12.36 ± 0.2 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

5. The process of claim 1 wherein X is selected from the group consisting of aluminum, boron, gallium and combinations thereof and Y is selected from the group consisting of silicon, germanium and combinations thereof.

6. The process of claim 1 wherein X comprises aluminum and Y comprises silicon.

7. The process of claim 1 wherein said crystalline material has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB and VIII of the Periodic Table.

8. The process of claim 1 wherein said catalyst composition has been thermally treated at a temperature up to about 925° C. in the presence or absence of steam.

9. The process of claim 7 wherein said catalyst composition has been thermally treated at a temperature up to about 925° C. in the presence or absence of steam.

10. The process of claim 1 wherein said catalyst composition comprises said synthetic porous crystalline material and a matrix.

11. The process of claim 10 wherein said matrix is silica or alumina-containing material.

12. The process of claim 10 wherein said catalyst composition is in the form of extrudate, beads or fluidizable microspheres.

13. The process of claim 1 wherein the olefin feed contains a mixture of light olefins.

14. The process of claim 1 wherein the olefin component of the feed contains from two to seven carbon atoms.

15. The process of claim 1 wherein the olefin feed contains at least one olefin selected from the group consisting of ethylene, propylene, butenes, pentenes, hexenes and heptenes.

16. The process of claim 1 wherein the olefin feed contains propylene.

17. The process of claim 1 wherein the olefin feed contains butene.

18. The process of claim 1 wherein the olefin feed is naphtha cracker off-gas containing light olefins.

19. The process of claim 1 wherein the olefin feed is light catalytic cracked gasoline containing pentenes, hexenes and heptenes.

20. The process of claim 1 wherein the temperature is from about 50° to about 300° C.

21. The process of claim 1 wherein the total pressure is at least about 5 atmospheres.

22. The process of claim 1 wherein the mole ratio of water to total olefin is from about 0.1 to about 30.

23. The process of claim 1 wherein said olefin hydration catalyst comprises an additional material incorporated with said synthetic porous crystalline material, wherein said additional incorporated material possesses catalytic activity with respect to olefin hydration.

* * * * *